United States Patent [19]

Gallis

[11] Patent Number: 4,923,802
[45] Date of Patent: May 8, 1990

[54] PEPTIDE SUBSTRATES FOR THE DETECTION, CHARACTERIZATION AND PURIFICATION OF PROTEIN KINASE C

[75] Inventor: Byron M. Gallis, Seattle, Wash.

[73] Assignee: Immunex Corporation, Seattle, Wash.

[21] Appl. No.: 744,498

[22] Filed: Jun. 13, 1985

[51] Int. Cl.$^5$ .............................................. C12Q 1/48
[52] U.S. Cl. ..................................... 435/15; 435/810; 530/326; 530/327; 530/328; 530/329; 530/330
[58] Field of Search ................... 435/194, 15, 18, 810, 435/68; 530/326, 327, 328, 329, 330

[56] References Cited

PUBLICATIONS

Lehninger Al, *Biochemistry* 2nd Edition, pp. 71–76.
Ferrari, S. et al., *FEBS Lett.*, vol. 184, No. 1, pp. 72–77, (May 1985).
Shackelford, D. A. and I. A. Trowbridge, "Induction of Expression and Phosphorylation of the Human Interleukin 2 Receptor by a Phorbol Diester," *J. Biol. Chem.*, 259:11706 (1984).
Wise, Bradley C. et al., "Phospholipid–Sensitive Ca2+–Dependent Protein Kinase from Heart, II, Substrate Specificity and Inhibition by Various Agents," *J. Biol. Chem.*, 257:8489 (1982).
Leonard, Warren J., "Molecular Cloning and Expression of cDNAs for the Human Interleukin–2 Receptor," *Nature* 311:626 (1984).
Ramachandran, Chidambaram et al., "Phosphorylation of High Mobility-Group Proteins by the Calcium–Phospholipid-Dependent Protein Kinase . . . " *J. Biol. Chem.* 259:13495 (1984).
Hunter, et al., "Protein Kinase C Phosphorylation of the EGF Receptor at a Threonine Residue Close to the Cytoplasmic Face of the Plasma Membrane", *Nature* 311:480 (1984).
Niedel, et al., "Phorbol Diester Receptor Copurifies with Protein Kinase C", *Pro. Natl. Acad. Sci. U.S.A.* 80:36 (1983).
Castagna, et al., "Direct Activation of Calcium-Activated, Phospholipid-Dependent Protein Kinase by Tumor-Promoting Phorbol Esters", *J. Bio. Chem.* 257:7847 (1982).
Leach, et al., "Characterization of a Specific Phorbol Ester Aporeceptor in Mouse Brain Cytosol", *Proc. Natl. Acad. Sci. U.S.A.* 80:4208 (1983).
Parker, et al., "Purification to Homogeneity of Protein Kinase C from Bovine Brain–Identity with the Phorbol Ester Receptor", *EMBO Journal* 3:953 (1984).

*Primary Examiner*—Robert J. Warden
*Assistant Examiner*—Toni R. Scheiner

[57] ABSTRACT

A highly specific peptide substrate for protein kinase C is composed in basic form of a serine or threonine amino acid residue flanked by groups of basic amino acids composed entirely of argenine, lysine or histidine or any combination of these amino acid residues. The peptide, which is phosphorylated by the protein kinase C, can be used in a direct or competitive assay for protein kinase C by employing radiolabeled ATP. In the phosphorylation process the phosphate is transferred from the ATP by the protein kinase C to the peptide of the present invention.

19 Claims, No Drawings

PEPTIDE SUBSTRATES FOR THE DETECTION, CHARACTERIZATION AND PURIFICATION OF PROTEIN KINASE C

TECHNICAL FIELD

The present invention relates to an assay for protein kinase C, and more specifically to peptide substrates for the detection, characterization and purification of protein kinase C.

BACKGROUND OF THE INVENTION

Protein kinase C is a recently discovered enzyme found to phosphorylate basic proteins such as protamine and histone and other proteins. The phosphorylation of a protein may cause a functional change, which is generally a decrease or increase in enzymatic activity. Although protein kinase C is found in highest concentrations in the brain and spleen, it exhibits neither tissue nor species specificity.

Unlike other protein kinases, activation of protein kinase C is not dependent upon cyclic nucleotides, but activation does require phospholipid, diacylglycerol and calcium for maximum activity in vitro. Although diacylglycerol typically is not present in sufficiently high concentrations in cells to activate protein kinase C, it is transiently generated by the breakdown of phosphatidylinositol which is cleaved by phopholipase C, which in turn is activated when cells are stimulated by extra-cellular messengers. Such messengers include histamine, mitogens, growth factors, lymphokines, epinephrine, acetylcholine, vasopressin, gastrin and thrombin. With the breakdown of phosphatidylinositol, an intracellular increase in calcium ($Ca^{2+}$) occurs. The calcium acts not only independently of and upon, but also synergistically with protein kinase C to produce many of the same physiological responses initiated by the increase in phosphatidylinositol turnover by extra-cellular messengers.

It has recently been found that tumor promoting phorbol diesters can substitute for diacylglycerol as activators for protein kinase C both in vitro and in vivo. The activities of phorbol diesters are mediated through protein kinase C which in actuality serves as a receptor for the phorbol diester. Phorbol diesters are tumor promoters, and induce tumor formation when administered with a carcinogen. When administered to cells in culture, phorbol diesters may induce transformation-like phenotypes or differentiation. It is known that cells possess high affinity, saturable, stereospecific receptors for phorbol diesters. The foregoing raises the possibility that protein kinase C, already known to be involved in normal cellular responses to external physiological signals, likely plays a role in the activities of tumor promoters, such as phorbol diesters. Thus, increased knowledge concerning the enzymology of protein kinase C may lead to a greater understanding of the actions of tumor promoters.

As mentioned above, protein kinase C phosphorylates a variety of basic proteins and a number of protein substrates. The following parameters are important in determining the "goodness" of a phosphorylation carried by protein kinase C: (a) phosphorylation is stoichiometric, i.e., at least 1 mole of phosphate is incorporated per mole of substrate; (b) one, two or three discrete sites on the protein molecule are phosphorylated, each in a stoichiometric manner; and, (c) the reaction is relatively rapid, usually completed within seconds or minutes, and occasionally as long as one hour. In efficient phosphorylation by protein kinase C, the Michaelis-Menten constant ($K_m$) should be in the micromolar range and the maximum reaction rate ("$V_{max}$") should be between about 5 and 50 micromoles ("umole") $PO_4$ transferred per min. per mg of protein.

The various in vitro phosphorylations catalized by protein kinase C include phosphorylation of guanylate cyclase, which causes an increase in its activity. The tumor-promoter TPA (12-0-tetradecanoylphorbol-13-acetate) also increases both guanylate cyclase activity, and cyclic GMP levels when added to lymphocytes. Thus it appears that protein kinase C phosphorylation of guanylate cyclase in vitro and in the cell increases this enzyme's activity. Protein kinase C cataylizes phosphorylation of 3-hydroxy-3-methylglutonyl coenzyme A reductase (HMG-CoA reductase), which is the rate-limiting enzyme in the cholesterol biosynthesis pathway. The protein kinase C-induced phosphorylation inactivates HMG-CoA reductase. Protein kinase C activates through phosphorylation tyrosine hydroxylase, which is a rate-limiting enzyme in the biosynthesis of catecholamines. The site of phosphorylation of the substrate appears to be the same to that of cAMP-dependent protein kinase. Protein kinase C also phosphorylates smooth muscle heavy meromyosin, thereby decreasing its actin-activated Mg-ATPase activity. In this situation, the site of phosphorylation by protein kinase C is different than the site of phosphorylation by cAMP-dependent protein kinase. Addition of protein kinase C to cardiac sarcoplasmic reticulum causes phosphorylation of phospholambin and $Ca^{2+}$ uptake with the site of phosphorylation being different than that of cAMP-dependent protein kinase and calmodulin-dependent protein kinase. Further, protein kinase C phosphorylates glycogen synthetase, thereby inactivating this rate-limiting enzyme for glycogen synthesis. There are many sites phosphorylated on glycogen synthetase by a variety of protein kinases, including cAMP-dependent protein kinase. However, relative to these other protein kinases, phosphorylation by protein kinase C is uniquely selective.

Protein kinase C has been found to phosphorylate the basic nuclear proteins of the high-mobility group (HMG), protein 14 and 17. Protein kinase C phosphorylates a single site on HMB 17, Gly-Arg-Arg-Ser (P) Ala-Arg-Leu-Ser-Ala-Lys and also a single site on HMG 14, Pro-Lys-Arg-Arg-Ser (P) Ala-Arg-Leu (the "(P)" indicating the site of phosphorylation). cAMP-dependent protein kinase phosphorylates these basic nuclear proteins but not at the same locations phosphorylated by protein kinase C.

Perhaps the most extensively-studied receptor for a polypeptide growth factor is the epidermal growth factor (EGF) receptor. The receptor is itself a tyrosine protein kinase, a transmembrane protein with a domain that binds external EGF and a cytoplasmic domain that encodes a protein kinase activity. When bound by EGF, this kinase undergoes an intramolecular tyrosine auto-phosphorylation which causes partial activation of enzyme. Protein kinase C has been found to phosphorylate the EGF receptor thereby causing an increase in serine and threonine phosphorylation, but a decrease in tyrosine phosphorylation. Hunter et al., 1984 Nature 311: 480–483, have identified the major site of phosphorylation of the EGF receptor by protein kinase C through the use of a peptide composed of the following 24 amino acids corresponding to residues 643-646 of the receptor: Trp-Leu-Arg-Arg-Arg-His-Ile-Val-Arg-Lys-Arg-Thr (P) Leu-Arg-Arg-Leu-Leu-Gln-Glu-Arg-Glu-Leu-Val-Glu. Hunter et al. used this synthetic peptide as a substrate for protein kinase C. The relatively long length of this peptide indicates that its secondary structure most likely is a factor in its ability to function as an efficient substrate for protein kinase C.

SUMMARY OF THE INVENTION

The present invention relates to a novel peptide substrate which is highly specific for the enzyme protein kinase C. Protein kinase C phosphorylates basic and other types of proteins thereby causing a functional change of the protein which is typically a decrease or increase in enzymatic activity. The peptide of the present invention is defined by the following formula:

$$H_2N-A_n-X_1-A_n-COOH$$

wherein:

A represents a basic amino acid residue;
n is 1, 2, 3, 4 or 5; and
$X_1$ represents a serine (Ser) or threonine (Thr) residue.

Phosphorylation of the peptide of the present invention occurs at the $X_1$ site, i.e., at the serine or threonine residue. The phosphorylated serine or threonine residue is flanked by groups of basic amino acids, $A_n$, which may include from one to five arginine, lysine or histidine residues. The basic amino acid groups may be composed entirely of arginine, lysine or histidine or any combination of these amino acids.

In a further aspect of the present invention the peptide substrate may include additional outer groups of basic amino acids coupled to either or both of the amino and carboxyl terminals of the basic peptide defined by the formula set forth above. The outer groups of amino acids are coupled to the basic peptide with one to four spacer amino acid residues composed of any amino acid residues except for $X_1$. The outer groups of amino acids may be composed entirely of the basic residues arginine, lysine or histidine or any combination of these amino acids.

The peptide substrate of the present invention may also include additional amino acid residues coupled to either or both of the amino or carboxyl terminals of the peptide having one or more of the outer groups of basic amino acids as described in the foregoing paragraph. The additional residues may be of any composition except they may not be composed of a serine or threonine residue flanked on both sides by basic amino acids, whether the flanking basic amino acids are part of the other groups of basic amino acids or part of the additional amino acids. Preferably, from one to four additional amino acids may be employed at either or both terminals of the peptide.

Further aspects of the present invention include a kit and method for assaying for the presence of protein kinase C using the peptide having the above-described composition. The assay is based on the highly "efficient" phosphorylation of the peptide substrate by protein kinase C in the presence of ATP and enzyme activating agents. By employing radiolabeled ATP, the extent to which the peptide is phosphorylated by the protein kinase C may be readily measured, which measurement is indicative of the quantity of protein kinase C present in the sample being assayed. The kit includes radiolabeled ATP, the peptide substrate of the present invention, and agents for activating protein kinase C, which agents include $Ca^{2+}$, phospholipid and diacylglycerol. In the assay procedure, the sample to be tested is mixed together with a known quantity of peptide, radiolabeled ATP, $Ca^{2+}$, phospholipid and diacylglycerol. The extent to which phosphate is transferred from the ATP by the enzyme to the peptide is determined by measuring the radioactivity of the phosphorylated peptide substrate. As an illustrative, but not limiting example, this measurement can be made by binding the labeled peptide to a phosphocellulose filter and then measuring the radioactivity of the filter in a liquid scintillation spectrometer.

DETAILED DESCRIPTION

The present invention includes a relatively short peptide which functions as a highly specific substrate for protein kinase C, which is a $Ca^{2+}$, phospholipid-dependent protein kinase. The peptide substrate is phosphorylated by protein kinase C. As such, by radiolabeling the peptide, phosphorylation may be detected by binding the labeled peptide to a phosphocellulose filter and then measuring the level of radioactivity associated with the filter thereby ascertaining the level of protein kinase C present.

The protein kinase C substrate peptide of the present invention is defined by the following formula:

$$H_2N-A_n-X_1-A_n-COOH \qquad\qquad I.$$

wherein:

A represents a basic amino acid residue;
n is 1, 2, 3, 4 or 5; and,
$X_1$ represents a serine or threonine residue.

Phosphorylation of the peptide represented by formula I above occurs at $X_1$, i.e., at the serine or threonine residue. The phosphorylated residue is flanked on both the aminio-terminal side and the carboxyl-terminal side by groups of basic amino acids, "A", which may include from one to five arginine, lysine or histidine residues. These basic amino acid groups may be composed entirely of arginine, lysine or histidine or any combination of these amino acids.

The peptide substrate of the present invention may include a third group of basic amino acids designated as "B", coupled to the amino-terminal of the peptide, as represented by formula II below, by one or more spacer residues $X_2$. The third group of basic amino acids, B, also may be composed entirely of arginine, lysine or histidine, or any combination thereof. The spacer residue(s) $X_2$ may be composed of from 1 to 4 amino acid residues of any composition except the particular residue composing $X_1$. The peptide substrate of the present invention having the third group of amino acid residues incorporated therein may be represented by the formula:

$$H_2N-B_n-X_2-A_n-X_1-A_n-COOH \qquad II.$$

wherein:

A, n and $X_1$ are defined in formula I above;
B represents from 1 to 5 basic amino acid residues; and,
$X_2$ represents from 1 to 4 amino acid residue(s) of any composition(s) except $X_1$.

The peptide substrate of the present invention may also include from 1 to 4 additional amino acid residues coupled to either or both the amino and carboxyl-terminals of the peptide defined by formula II above. These additional residues may be of any composition except a serine or threonine residue flanked on both sides by one or more basic amino acids, whether these flanking amino acids are part of $B_n$, $A_n$ or the additional amino acids.

The peptide substrate of the present invention may include a fourth group of basic amino acids, designated as ("C") coupled to the carboxyl-terminal side of the peptide represented by formula I by one or more linking amino acid residues, designated as "$X_3$." This fourth group of basic amino acids, C, also may be composed entirely of arginine, lysine or histidine, or any combination thereof. The spacer residue(s) $X_3$ may be composed of from 1 to 4 amino acid residues of any composition except the particular residue composing $X_1$. In a manner similar to formula II above, the peptide substrate of the present invention having the fourth group of amino acid residues incorporated therein may be represented by the formula:

$$H_2N-A_n-X_1-A_n-X_3-C_n-COOH \qquad III.$$

wherein:

A, n and $X_1$ are as defined in formula I above;

C represents from 1 to 5 basic amino acid residues; and, $X_3$ represents from 1 to 4 amino acid residues of any composition except $X_1$.

In a manner analogous to the peptide substrate defined by formula II above, the peptide substrate defined by formula III may also include from 1 to 4 additional amino acid residues coupled to one or both the amino or carboxyl-terminals of the peptide. These additional residues may be of any composition except a serine or threonine residue flanked on both sides by one or more basic amino acids, whether these flanking amino acids are part of $A_n$, $C_n$ or the additional amino acids.

It is also within the scope of the present invention to provide a peptide substrate having both the third and fourth groups of basic amino acids coupled to the amino-terminal side and carboxyl-terminal side of the peptide represented by formula I through one or more linking amino acid residues, $X_2$ and $X_3$, respectively. The amino acids composing such third and fourth groups are the same basic residues discussed above in relationship to the peptides represented by formulas II and III, i.e., arginine, lysine or histidine, or any combination thereof. Likewise, the spacer residues $X_2$ and $X_3$ are composed of from 1 to 4 amino acid residues of any composition except for serine or threonine. The peptide substrate of this construction may be represented by the following formula:

$$H_2N-B_n-X_2-A_n-X_1-A_n-X_3-C_n-COOH \qquad IV.$$

wherein:

A, n and $X_1$ are as defined in formula I above;

B and $X_2$ are defined as in formula II above; and,

C and $X_3$ are defined as in formula III above.

In a manner similar to the peptide substrates defined by formulas II and III above from 1 to 4 additional amino acid residues may be coupled to one or both of the amino and carboxyl terminals of the peptide substrate defined in formula IV. These additional residues may be of any composition except a serine or threonine flanked on both sides by one or more basic amino acid residues, whether these flanking amino acids are part of $B_n$, $C_n$ or the additional amino acids.

In a preferred form of the present invention, $X_1$ is composed of serine, $A_n$ is composed of the basic amino acids arginine and lysine, and n is equal to 2, resulting in the following peptide composition: $H_2N$-Arg-Lys-Ser-Arg-Arg-COOH. In other examples of preferred forms of the present invention, the peptide substrate represented by formula II may be of the following composition: $H_2N$-Arg-Arg-$X_2$-Arg-Lys-Ser-Arg-Arg-COOH, and the peptide substrate represented by formula IV may be of the following composition: $H_2N$-Gln-Arg-Arg-$X_2$-Arg-Lys-Ser-Arg-Arg-Thr-Ile.

Ideally the number of amino acids composing the peptide substrates of the present invention are kept to a minimum while still being highly specific for protein kinase C. It will be appreciated that as the number of amino acid residues composing the peptide substrates of the present invention is increased, the production of the peptide, such as by chemical synthesis, is rendered substantially more difficult, time-consuming and expensive. To this end, preferably the number of basic amino acid residues represented by the designations A, B and C in formulas I - IV above is either 2 or 3. Likewise, ideally a single amino acid residue is employed for $X_2$ and $X_3$. In addition preferably the number of additional amino acids added to the terminals of the peptide substrate defined by formula II, or to the terminals of the peptide substrate defined by formula III, or to the terminals of the peptide substrate defined by formula IV is also minimized. It will be appreciated that peptide substrates composed in this manner are sufficiently short so that secondary or tertiary structural effects are not involved in the site recognition of the protein kinase C by the peptide substrate. Rather, the site recognition is dependent upon the primary structure, amino acid composition and positive charge state of the peptide substrate. As such, protein kinase C can be expected to have a fairly specific substrate specificity toward the peptide compositions of the present invention.

As discussed above, the serine residue of the peptide substrate of the present invention is phosphorylated by protein kinase C in accordance with the following equation:

$$\text{Peptide} + \text{ATP} \xrightarrow[\text{phospholipid, diacylglycerol}]{\text{protein kinase C, Ca}^{2+}} \qquad V.$$

$$\text{Peptide-Phosphate} + \text{ADP.}$$

Also as previously noted, protein kinase C employed in formula V is activated in the cell by diacylglycerol which in turn is transiently generated by the breakdown by phosphatidylinositol resulting from stimulation of cells by extra-cellular messengers, such as histamine, mitogens, growth factors, epinephrine, acetylocholine, vasopressin, gastrin and thrombin. As discussed more fully below, the phosphorylated peptide in formula V provides a straightforward and accurate technique for assaying for the presence of protein kinase C.

The peptide substrate of the present invention as defined in formulas I through IV above can be produced by several different methods, such as by recombinant DNA methods or chemical synthesis. If recombinant DNA methods are used, a synthetic oglionucleotide corresponding to the amino acid sequence of the peptide can be produced by well-known techniques, such as by phosphodiester or triester methods. The details of the triester synthesis technique are set forth in Sood et al., 1977 *Nucl. Acid Res.* 4: 2557; and, Hirose et al., 1978, *Tet. Lett.* 28: 2449. The synthetic oglionucleotide can then be inserted within a cloning vector, such as a plasmid or bacteriophage, which in turn may be employed to transform a compatible prokaryotic or eukaryotic host for replication of the vector and expression of the peptide. Recombinant DNA techniques for producing various protein products, such as the peptide of the present invention are now well known as set forth in the editorial and supporting papers of Vol. 196 of *Science* (April 1977).

As an alternative to the foregoing, the peptide substrate of the present invention can be chemically synthesized by well known techniques. Of preference is the solid phase technique developed by R. B. Merrifield which permits the peptide to be built residue by residue from the carboxyl terminal amino acid to the amino terminal amino acid either manually or with an automated, commercially available synthesizer. Details of the solid phase technique are well known, such as set forth in B. Gutte and R. B. Merrifield, *J. An. Chem. Soc.*, 91: 501 (1969); G. Barany and R. B. Merrifield, *The Peptides*, Vol. 2 (E. Gross and J. Meienhoffer eds.) Academic Press, New York (1979).

For use with the peptide substrate of the present invention, protein kinase C can be prepared by standard techniques, such as described by Kikkawa et al., *Methods in Enzymology*, (Corbin and Hardman, eds.) 94: 288 (1983); Le Peuch et al., *Proc. Natl. Acad. Sci. U.S.A.* 99: 6858 (1983). The primary source of protein kinase C is a homogenate from rat brains. The protein kinase C is removed from the supernatant centrifuged from homogenized rat brains by anion exchange chromatography. Applicant has found that a suitable column matrix for this purpose is DEAE-Sephacel. The DEAE-Sephacel column is equilibrated with a buffer and then the supernatant applied to the column. The column is then washed with the starting buffer and then elution is carried out with a linear salt gradient in the same buffer. Fractions are collected and assayed as generally described below and as detailed in Example 2 infra. The assayed fractions found to contain protein kinase C activity are pooled and further concentrated by salt precipitation. Applicant has determined that the ammonium sulfate may be advantageously employed for this purpose. The resulting precipitate is dissolved in a buffer and then the protein kinase C contained therein is further purified on a gel column. Applicant has determined that a suitable column for this process is Ultrogel AcA34. Preferably the column is equilibrated with a buffer prior to application of the protein kinase C sample and then eluted with the same buffer.

The peptide substrate of the present invention may be employed to assay for the presence of protein kinase C, for instance, during the above-outlined process of preparing the enzyme. The assay is based on the phosphorylation of the peptide substrate by protein kinase C. In the assay, the sample to be tested is mixed together with the peptide substrate, radiolabeled ATP, $Ca^{2+}$, phospholipid and diacylglycerol. The mixture is incubated for only a brief period to insure linearity of the reaction and then spotted onto phosphocellulose filter paper. The level of radioactivity on the filter is measured, for instance by liquid scintillation spectrometry. The level of radiation is indicative of the extent to which the substrate has been phosphorylated, which in turn is indicative of the amount of protein kinase C present in the sample being assayed. As can be appreciated, by use of the peptide substrate for the present invention, the presence of protein kinase C may be conveniently and rapidly assayed.

By employing the peptide substrates of the present invention at a concentration of about 20 uM, the peptide is phosphorylated to completion in about 20 minutes. The $K_m$ and $V_{max}$ of the phosphorylation reaction are respectively approximately 23 uM and 77 nmole $PO_4$/min/mg. At a peptide concentration of 1 mM, the reaction rate is 80 pmole $PO_4$/min and is linear for at least 40 min.

Phosphorylation reactions were carried out with other peptide compositions to compare the specificity of protein kinase C for the peptide substrate of the present invention relative to such other peptides. In a phosphorylation reaction with the synthetic peptide: Leu-Arg-Arg-Ala-Ser-Leu-Gly (known as Kemptide) the rate of phosphorylation was found to be 20 pmole $PO_4$/min. at a peptide concentration of 1 mM. However, the enzyme was not saturated with substrate, even at a concentration of 3 mM peptide. This indicates that the $K_m$ is so high that it could not be determined. Kemptide is the physiological site of phosphorylation of pyruvate kinase by cAMP-dependent protein kinase.

Phosphorylation by protein kinase C also has been carried out with the synthetic peptide of the following composition: Arg-Arg-Lys-Ala-Ser-Gly-Pro-Pro-Val. See O'Brian et al., Biochem. Biophys. Res. Commun., 124: 296 (1984). Although this peptide is closely related to Kemptide, it was not as good a substrate for protein kinase C. The $K_m$ of the reaction was 130 uM and rate of reaction was 8 pmole $PO_4$/min peptide at a concentration of 450 μM.

The ability of the catalytic subunit of cAMP-dependent protein kinase to phosphorylate the peptide substrate of the present invention was also investigated. Under optimal conditions, peptide substrate concentrations as high as 300 uM did not saturate the enzyme, thereby suggesting that the $K_m$ of cAMP-dependent protein kinase is in excess of 300 uM for the peptide of the present invention. The rate of reaction was only 60 pmole $PO_4$/min. at a peptide concentration of 300 uM. In contrast, the peptide of the present invention was phosphorylated by protein kinase C at a rate of 60 pmole $PO_4$/min substrate at a concentration of 20 uM. The very significant difference in reaction rates between protein kinase C and cAMP-dependent protein kinase emphasizes the high specificity of protein kinase C to peptide substrate of the present invention. This specificity is also born out by the above-discussed inability of protein kinase C to effectively phosphorylate peptides which are substrates for other types of protein kinases.

The peptide substrate of the present invention also may be employed in a competitive inhibition assay with protein substrates for protein kinase C. The $K_m$ of protein kinase C for some of its protein substrates, as discussed above, is in the range of 1 to 10 uM. The $K_m$ of protein kinase C for the peptide substrate of the present invention is in the range of 20-25 uM. As such, much higher concentrations of the peptide substrates may be used to assay for protein kinase C, at least up to 1 mM, without causing inhibition of the enzyme. At these higher concentrations the peptide substrate is able to effectively compete against protein substrates for protein kinase C. Using a fixed concentration of protein substrate together with protein kinase C, radio-labeled ATP, the $Ca^{2+}$, phospholipid and diacylglycerol, increasing concentrations of peptide substrate can be added to the reaction mixture. The inhibition of phosphorylation of the protein substrate is monitored by fractionation of the mixture of an SDS polyacrylamide gel followed by autoradiography of the gel to localize the protein substrate and quantify the degree of inhibition of the protein substrate caused by the peptide substrate. This information provides valuable information regarding the enzymology of protein kinase C and the ability of the peptide substrate of the present invention to be used in competitive assays for measuring the quantity of various protein substrates to protein kinase C present in a particular sampling being tested.

The processes and products of the present invention are further illustrated by the following examples.

EXAMPLE 1

Preparation of Peptide Substrate

Solid phase chemical synthesis according to the general method developed by Merrifield, supra, is employed to prepare peptide substrates having the following compositions:
a. $H_2N$-Arg-Lys-Ser-Arg-Arg-COOH
b. $H_2N$-Arg-Arg-Gln-Arg-Lys-Ser-Arg-Arg-COOH
c. $H_2N$-Gln-Arg-Arg-Gln-Arg-Lys-Ser-Arg-Arg-COOH

EXAMPLE 2

Preparation of Protein Kinase C

Protein kinase C was prepared from the brains of eight rats each having a weight of from 150 to 200 grams. The rats are sacrificed by cervical dislocation. The brains of the rats are removed and placed in eight volumes of ice-cold buffer A (40 ml), composed of the following: 20 mM 4-(2-hydroxyethyl)-1-piperazineethanesulfonic acid ("HEPES"), pH 7.5; 0.3 M sucrose; 2 mM ethyl-enediaminetetracetic acid ("EDTA"); 10 mM ethylene glycol bis( B -aminoethylether)-N, N, N', N'-tetraacetic acid ("EGTA"); 2 mM dithiothreitol ("DDT"); 1 mM phenylmethylsulfonyl; 10 ug/ml pepstatin A; 10 ug/ml soybean tripsyn inhibitor; 10 ug/ml leupeptin; and 10 uM E-64 (Peninsula Labs). E 64 is an inhibitor of $CA^{2+}$-activated proteases. The brains are homogenized with 5 strokes of teflon-glass homogenizer and centrifuged for one hour at $100,000 \times g$ in a Ti 75 rotor. The resulting supernatant is saved and adjusted to a conductivity of 0.7–0.9 mmho. The supernatant is then loaded onto a 35 ml DEAE-Sephacel column (Pharmacia Fine Chemicals) which has been previously equilibrated with buffer B of the following composition: 20 ml HEPES, pH 7.5; 2 mM EGTA; 2 mM EDTA; and, 2 mM DDT. Thereafter the column is washed at a flow rate of 30 ml/hr with ten column volumes of buffer B, followed by two column volumes of the same buffer in 0.1% Triton X-100. Lastly, the column is washed with two additional column volumes of buffer B. The protein kinase C is eluted from the column with 400 ml gradient of from 0 to 0.3 M NaCl in buffer B. Every fifth fraction (4.0 milliliter volume) is assayed as described below in Example 3.

Fractions containing activity are pooled and precipitated with ammonium sulfate to 70% saturation. The precipitation is allowed to sit for 30 minutes on ice and then is sedimented by centrifugation at $20,000 \times g$ for 15 minutes at 4° C. The precipitate is then dissolved in 3 ml of buffer C of the following composition: 20 mM HEPES, pH 7.5; 0.5 mM EDTA; 0.5 mM EGTA; and, 2 mM DDT. The dissolved precipitate is applied to a column of an Ultrogel 2.5 cm $\times$ 95 cm containing ultrogel ACA 34 (LKB Instruments), previously equilibrated with buffer C. Elution is carried out with buffer C applied to the column in a flow rate of 12 ml/hr. One hundred 2 ml fractions are collected and assayed. Peak fractions are pooled, and an equal volume of glycerol is added thereto. The solution is made 10 ug/ml pepstatin A, 10 ug/ml leupeptin, 10 uM E-64 and 10 ug/ml soybean tripsyn inhibitor. The resulting enzyme may be stored at -20° C. for at least five months.

EXAMPLE 3

Direct Assay for Protein Kinase C Using Peptide Substrate

Samples putatively containing protein kinase C are assayed using the following mixture: 20 mM HEPES, pH 7.5; 10 mM $MgCl_2$; 1.5 mM $CaCl_2$; 2 ug phosphatidyl-L-serine (Sigma Chemical Company, P6641); 0.3 ug diolein (88% 1.3 isomer at 15% 1.2 isomer, Sigma Chemical Company, D3380); 2 mM DDT; 200 uM (gamma$^{32}$P) ATP (specific activity 200-1000 cpm/picomole); 5 ul (1.5 ug) protein kinase C sample; and, 25 uM peptide substrate (from Example 1). The above mixture is incubated at 30° C. for five minutes in a volume of 50 microliters. This brief incubation period insures linearity of the reaction.

To quantify the protein kinase at present in the sample being tested, 10 ul of the reaction mixture is spotted onto a 2 centimeter square of Whatman P81 phosphocellulose paper. Thereafter the paper is washed three times in 0.5 (vol/vol) phosphoric acid (10 mililiter per square paper) for 2 minutes per wash. The filter is then dried with a heat gun and immersed in a vial in toluene POPOP and then counted in a liquid scintillation spectrometer (Minaxi Tri-carb 4000, United Technologies/Packard). By this procedure applicant ascertained that the protein kinase C has a $V_{max}$ for phosphorylation of the synthetic peptide sequence Gln-Arg-Arg-Gln-Arg-Lys-Ser-Arg-Arg-Thr-Ile of approximately 77 nmole $PO_4$/min/mg and a $K_m$ of approximately 23 uM.

EXAMPLE 4

Assay for Protein Kinase C with 1 mM Synthetic Peptide

The assay for protein kinase C specified in Example 3 is repeated with the exception that 1 mM of synthetic peptide was employed. Under these conditions the reaction rate is 80 pmole $PO_4$/min and is linear for at least 40 minutes.

EXAMPLE 5

Assay for Protein Kinase C Using 20 uM Synthetic Peptide

The assay for protein kinase C set forth in Example 3 above is repeated with the exception of using 20 uM synthetic peptide. In this situation, the peptide is phosphorylated to completion within 20 min.

EXAMPLE 6

Assay for Protein Kinase C Using Kemptide

The assay procedure set forth in Example 3 above is employed in conjunction with the peptide substrate Kemptide having the following composition: Leu-Arg-Arg-Ala-Ser-Leu-Gly. This peptide constitutes the physiological site of phosphorylation of pyruvate kinase by cAMP dependent protein kinase. When employing a concentration of Kemptide of 1 mM, the rate of phosphorylation is 20 pmole PO$_4$/min. However, this substrate will not saturate the enzyme even at a substrate concentrations as high as 3 mM peptide, indicating that the K$_m$ is too high to be determined.

EXAMPLE 7

Assay For cAMP-Dependent Protein Kinase Using Synthetic Peptide of the Present Invention The following assay procedure is employed to ascertain the ability of cAMP-dependent protein kinase to phosphorylate the synthetic peptide composition of Example 1 above. The reaction mixture contains 10 mM MgCl$_2$, 20 mM HEPES, pH 7.5, 1 mM DTT, 200uM (gamma 32P) ATP (specific activity 1000 cpm/pmole), and 40 ng cAMP-dependent protein kinase. This mixture is incubated at 30° C. for five minutes in a volume of 50 ul. Use of the peptide of the present invention in a concentration as high as 300 uM will not saturate the cAMP-dependent protein kinase, which suggests that the K$_m$ of the enzyme is in excess of 300 uM. The rate of reaction is approximately 60 pmole PO$_4$/min. at a concentration of 300 uM peptide. The slow rate of reaction indicates that cAMP-dependent protein kinase is not highly specific for the peptide substrate of the present invention.

EXAMPLE 8

Comparative Inhibition of Protein Kinase C Using Peptide Substrate

The general assay procedure set forth in Example 3 above is employed to test the ability of the peptide substrate of the present invention to inhibit phosphorylation of protein substrates by protein kinase C. In the assay procedure, increasing concentrations of the peptide substrate of the present invention set forth in Example 1 above is added to the reaction mixture to compete for the protein kinase against a protein substrate present in the reaction. Generally, the affinity constant for the peptide substrate is between 2 and 20 times higher than that for individual protein substrates such as those set forth above in the Background of the Invention section of the present application.

In the assay procedure, a fixed concentration of 1 uM of interleukin-2 receptor is employed together with increasing concentrations of the receptor is employed together with increasing concentrations of the peptide substrate set forth in Example 1 above. The initial concentration of the peptide substrate is 25 uM, and the concentration is sequentially increased by 50 uM to a maximal concentration of 300 μM. After each incubation period for each concentration of protein substrate, the inhibition of phosphorylation of the protein substrate caused by the peptide substrate is monitored by fractionation of the reaction mixture on SDS-polyacramide gel followed by autoradiography of the gel to localize the protein substrate and measure the degree of inhibition of the protein substrate caused by the synthetic peptide. The electrophoresis was performed in 10% polyacrylamide slabs containing 0.1% SDS (w/v). The electrophoresis was performed for 4 hours at a 35 mA constant current at 25° C. By this assay procedure the degree of inhibition of the protein substrate caused by the synthetic peptide was found to be 80% at 100 μM peptide.

As will be apparent to those skilled in the art to which the invention is addressed, the present invention may be embodied in forms other than those specifically disclosed above without departing from the spirit or essential characteristics of the invention. The particular embodiments of the present invention, as described above, are therefore to be considered in all respects as illustrative and not restrictive. The scope of the invention is as set forth in the appended claims rather than being limited to the Examples in the foregoing description.

The embodiments of the invention in which an exclusive property or privilege is claimed are defined as follows:

1. A method for assaying for the presence of protein kinase C, comprising:
(a) reacting activated protein kinase C in the presence of ATP with a peptide substrate of the following formula:

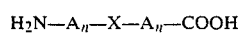

$$H_2N-A_n-X-A_n-COOH$$

wherein:
each A, which may be the same or different, represents a basic amino acid residue;
each n is independently selected from the integers 1 to 5; and,
X$_1$ represents a serine (Ser) or threonine (Thr) residue; and,
(b) measuring the extent to which the peptide substrate is phosphorylated, and
(c) determining the presence of protein kinase C based on the degree of phosphorylation of the peptide substrate.

2. A method according to claim 1, wherein A is selected from the group consisting of Arg and Lys.

3. The method according to claim 1, wherein the peptide substrate has the structure:

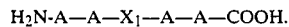

$$H_2N\text{-}A-A-X_1-A-A-COOH.$$

4. A method according to claim 3, wherein A is selected from the group consisting of Arg and Lys.

5. The method according to claim 4, wherein the peptide substrate has the structure:

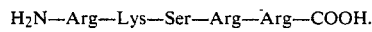

$$H_2N-Arg-Lys-Ser-Arg-Arg-COOH.$$

6. A method according to claim 1, wherein the ATP is radiolabeled and the extent to which the peptide substrate is phosphorylated is determined by measuring the radioactivity of the phosphorylated peptide substrate.

7. The method according to claim 6, wherein the radioactivity of the phosphorylated peptide substrate is measured by liquid scintillation counting.

8. A kit for assaying for the presence of protein kinase C, comprising the following packaged compositions:
(a) labeled ATP in a first container;
(b) agents for activating protein kinase C in a second container; and
(c) a peptide substrate phosphorylatable by protein kinase C in a third container, said peptide substrate represented by the formula:

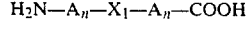

$$H_2N-A_n-X_1-A_n-COOH$$

wherein:
each A, which may be the same or different, represents a basic amino acid residue;
each n is independently selected from the integers 1 to 5; and,
X$_1$ represents a Ser or Thr residue.

9. The kit according to claim 8, wherein said ATP is radiolabeled.

10. The kit according to claim 8, wherein the activating agents for protein kinase C are selected from the group consisting of calcium, diacylglycerol and phospholipid.

11. A kit according to claim 8, wherein A is selected from the group consisting of Arg and Lys.

12. The kit according to claim 11, wherein said peptide substrate comprises a structure:

$$H_2N-A-A-X_1-A-A-COOH.$$

13. The kit according to claim 12, wherein said peptide substrate having the structure:

$$H_2N\text{-Arg-Lys-Ser-Arg-Arg-COOH}.$$

14. A method for assaying for the presence of protein kinase C, comprising:
(a) reacting activated protein kinase C in the presence of ATP with a peptide substrate selected from the group consisting of the following formulas:

$$H_2N-B_n-X_2-A_n-X_1-A_n-COOH,$$

$$H_2N-A_n-X_1-A_n-X_3-C_n-COOH, \text{ and}$$

$$H_2N-B_n-A_n-X_1-A_n-X_3-C_n-COOH$$

wherein:
each A, which may be the same or different, represents a basic amino acid residue;
$B_n$ represents from 1 to 5 basic amino acid residues;
$C_n$ represents from 1 to 5 basic amino acid residues;
each n is independently selected from the integers 1 to 5;
$X_1$ represents a serine (Ser) or threonine (Thr) residue;
$X_2$ represents from 1 to 4 amino acid residues of any composition except $X_1$; and,
$X_3$ represents from 1 to 4 amino acid residues of any composition except $X_1$.
(b) measuring the extent to which the peptide substrate is phosphorylated, and
(c) determining the presence of protein kinase C based on the degree of phosphorylation of the peptide substrate.

15. A method according to claim 14, wherein A is selected from the group consisting of Arg and Lys.

16. A method for assaying for the presence of protein kinase C, comprising:
(a) reacting activated protein kinase C in the presence of ATP with a peptide substrate selected from the group consisting of the following formulas:

$$H_2N-B_n-X_2-A_n-X_1-A_n-COOH,$$

$$H_2N-A_n-X_1-A_n-X_3-C_n-COOH, \text{ and}$$

$$H_2N-B_n-X_2-A_n-X_1-A_n-X_3-C_n-COOH$$

wherein:
each A, which may be the same or different, represents a basic amino acid residue;
$B_n$ represents from 1 to 5 basic amino acid residues;
$C_n$ represents from 1 to 5 basic amino acid residues;
each n is independently selected from the integers 1 to 5;
$X_1$ represents a serine (Ser) or threonine (Thr) residue;
$X_2$ represents from 1 to 4 amino acid residues of any composition except $X_1$; and,
$X_3$ represents from 1 to 4 amino acid residues of any composition except $X_1$;
said peptide substrate further comprising from one to four additional amino acid residues linked to either or both of the amino or carboxyl terminals of the peptide, wherein such additional residues do not include a Ser or Thr residue flanked by any basic amino acid residue; and
(b) measuring the extent to which the peptide substrate is phosphorylated, and
(c) determining the presence of protein kinase C based on the degree of phosphorylation of the peptide substrate.

17. A method according to claim 16, wherein the substrate is $H_2N$-Gln-Arg-Arg-Gln-Arg-Lys-Ser-Arg-Arg-Thr-Ile-COOH.

18. A packaged kit for assaying for the presence of protein kinase C, comprising the following compositions:
(a) labeled ATP in a first container;
(b) agents for activating protein kinase C in a second container; and
(c) a peptide substrate phosphorylatable by protein kinase C in a third container, said peptide substrate represented by the formula:

$$H_2N-B_n-X_2-A_n-X_1-A_n-COOH,$$

$$H_2N-A_n-X_1-A_n-X_3-C_n-COOH, \text{ and}$$

$$H_2N-B_n-X_2-A_n-X_1-A_n-X_3-C_n-COOH$$

wherein:
each A, which may be the same or different, represents a basic amino acid residue;
$B_n$ represents from 1 to 5 basic amino acid residues;
$C_n$ represents from 1 to 5 basic amino acid residues;
each n is independently selected from the integers 1 to 5;
$X_1$ represents a Ser or Thr residue;
$X_2$ represents from 1 to 4 of any amino acid residue except $X_1$; and
$X_3$ represents from 1 to 4 of any amino acid residues except $X_1$.

19. A kit according to claim 18, wherein B is selected from the group consisting of Arg and Lys.

* * * * *